(12) United States Patent
Tashiro et al.

(10) Patent No.: US 7,947,224 B2
(45) Date of Patent: May 24, 2011

(54) DEVICE FOR CALIBRATING A MICROORGANISM QUANTIFYING APPARATUS

(75) Inventors: Yoshikazu Tashiro, Aichi (JP); Tomonori Shimakita, Aichi (JP); Akinori Kinugawa, Kanagawa (JP); Hachirou Sasai, Kanagawa (JP); Hiroshi Nakajima, Kanagawa (JP); Yoshihisa Kobayashi, Aichi (JP); Tomoyuki Makise, Gifu (JP)

(73) Assignee: Matsushita Ecology Systems Co., Ltd., Aichi (JP)

( * ) Notice: Subject to any disclaimer, the term of this patent is extended or adjusted under 35 U.S.C. 154(b) by 167 days.

(21) Appl. No.: 11/889,106

(22) Filed: Aug. 9, 2007

(65) Prior Publication Data

US 2008/0254500 A1    Oct. 16, 2008

Related U.S. Application Data

(62) Division of application No. 10/484,814, filed on Jan. 30, 2004.

(51) Int. Cl.
*G01N 21/00* (2006.01)
(52) U.S. Cl. .................. 422/57; 359/585; 436/172
(58) Field of Classification Search .............. 422/57; 359/585; 436/172
See application file for complete search history.

(56) References Cited

U.S. PATENT DOCUMENTS

| | | | |
|---|---|---|---|
| 5,139,031 A | | 8/1992 | Guirguis |
| 5,552,272 A | * | 9/1996 | Bogart ........................ 435/6 |
| 5,578,459 A | | 11/1996 | Gordon et al. |
| 5,897,993 A | | 4/1999 | Sato et al. |
| 5,952,238 A | | 9/1999 | Tsuji et al. |
| 6,040,191 A | * | 3/2000 | Grow ......................... 506/12 |

FOREIGN PATENT DOCUMENTS

| | | |
|---|---|---|
| CN | 2345183 Y | 10/1999 |
| JP | 05-273217 | 10/1993 |
| JP | 5-273217 | 10/1993 |
| JP | 11-113562 | 4/1999 |
| WO | WO 87/02802 A | 5/1987 |
| WO | WO 98/20352 A | 5/1998 |

OTHER PUBLICATIONS

Surman et al., Comparison of microscope techniques for the examination of biofilms, Journal of Micrbiological Methods, vol. 25, 1996, p. 57-70.*

The Society for Antibacterial and Antifungal Agents, Japan Nenji Taikai Yoshishu, Dai 28 Kai (JP), The Society for Antibacterial and Antifungal Agents, Japan, May 22, 2001; p. 44./Cited in the International Search Report.

Chinese Office Action dated Jul. 29, 2005, with English translation.

* cited by examiner

*Primary Examiner* — Ralph Gitomer
(74) *Attorney, Agent, or Firm* — Kratz, Quintos & Hanson, LLP

(57) ABSTRACT

A microorganism-collecting chip, for efficiently collecting microorganisms from a test sample and accurately detecting and quantifying the collected microorganisms, comprises a filter for removing contaminants and a filter for trapping microorganisms. A microorganism-collecting kit comprises the foregoing microorganism-collecting chip and a suction filtration unit, which may be a negative pressure tube provided at an opening with a rubber stopper. The microorganism-collecting chip has a liquid specimen injection container for injecting a liquid specimen and a hollow needle capable of penetrating the rubber stopper mounted at the opening of the negative pressure tube. The liquid specimen injected into the liquid specimen injection container is suction-filtered with a pressure of the negative pressure tube. Contaminants are removed with the filter for removing contaminants, and microorganisms are trapped on a filter for collecting microorganisms. The microorganisms trapped on the filter for collecting microorganisms are then detected and quantified by using a unit including the filter for collecting microorganisms.

2 Claims, 5 Drawing Sheets

F I G. 1
(a)
(b)
(c)
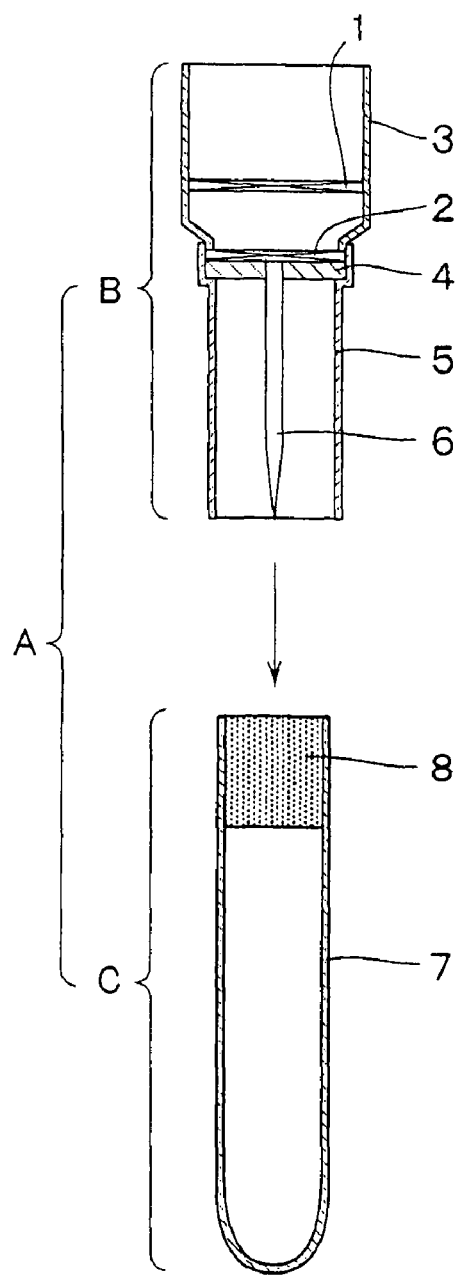
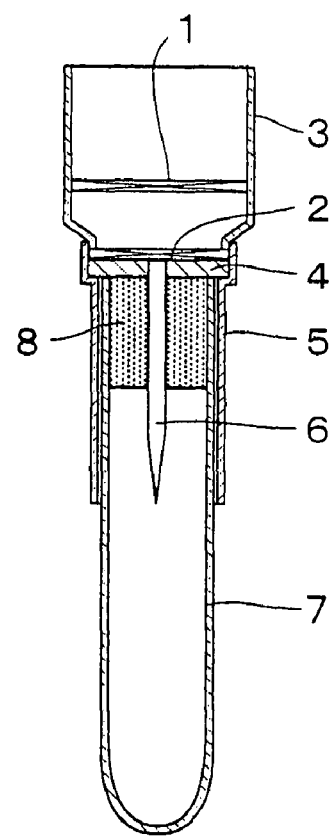
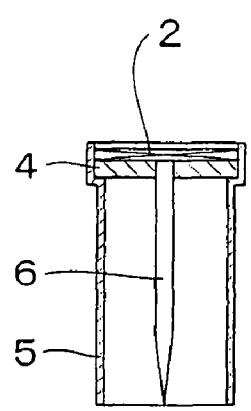

DEVICE FOR CALIBRATING A MICROORGANISM QUANTIFYING APPARATUS

CROSS REFERENCE TO RELATED APPLICATION

This is a Divisional Application of U.S. patent application Ser. No. 10/484,814, filed on Jan. 30, 2004, which is a 371 National stage application of PCT/JP02/07713, filed on Jul. 30, 2002, the prior applications being hereby incorporated by reference.

TECHNICAL FIELD

The present invention relates to a microorganism-collecting chip which is a unit for collecting microorganisms adhered to a test sample in which microorganisms are caused to color, luminesce or fluoresce to efficiently trap, detect and measure viable cells and dead cells or specific species of microorganisms present in the test sample, a microorganism-collecting kit, a method of quantifying microorganisms using this microorganism-collecting kit, a specimen for confirming a normal state of a microorganism-quantifying apparatus and a microorganism-quantifying apparatus.

BACKGROUND ART

As this type of the microorganism-collecting unit, there has been so far a unit in which microorganisms are filtered from a liquid specimen probably containing microorganisms by change of a pressure through operation of a pump to trap the microorganisms on a filter, after which the structure is disassembled to recover the filter with the collected microorganisms adhered using a tool capable of minute work, such as tweezers, for measurement of the microorganisms.

Such ordinary microorganism-collecting unit requires a large-sized device such as a pump. Further, in case of a specimen which is directly affected by contaminants or the like, a step of removing contaminants is separately needed. Moreover, it is necessary to recover the filter only for inspecting the microorganisms collected on the filter. Since this procedure requires a tool for performing minute work, such as tweezers, the efficiency is decreased, and a large amount of a sample cannot be treated. Further, an apparatus becomes large-sized because of the use of the pump. Thus, it cannot be used in a position of a narrow working space in a process of food inspection, etc. These require a certain inspection time and a certain technique in microorganism inspection which has to be performed quickly. Accordingly, this unit is problematic in that anybody cannot perform the inspection easily and quickly.

The invention is to solve these ordinary problems, and it is an object of the invention to provide a microorganism-collecting chip aimed at quick and easy operation by using a filter for removing contaminants integrated with a filter for collecting microorganisms.

Another object of the invention is to provide the microorganism-collecting chip wherein a pore diameter of the filter for removing contaminants is set at from 5 to 20 μm to pass microorganisms and remove the contaminants as much as possible, and a pore diameter of the filter for collecting microorganisms is set at from 0.2 to 0.8 μm to surely trap the microorganisms.

The other object of the invention is to provide the microorganism-collecting chip which can cope with a case of a large volume of a liquid specimen by providing a liquid specimen injection container with a filter for removing contaminants located on a bottom.

The other object of the invention is to provide the microorganism-collecting chip wherein a liquid specimen injection container is mounted ahead of the filter for removing contaminants and is adapted to be detachable from a site including the filter for removing contaminants, whereby the liquid specimen injection container can be used repeatedly.

The other object of the invention is to provide the microorganism-collecting chip wherein a lid with a swab for covering an opening of the liquid specimen injection container is added, whereby microorganisms can easily be collected from a position hard to collect the microorganisms, such as a corner or a gap in a test sample.

The other object of the invention is to provide the microorganism-collecting chip wherein the site including the filter for collecting microorganisms is adapted to be solely removable, whereby the filter for collecting microorganisms can be mounted on a microorganism-quantifying apparatus along with the site.

The other object of the invention is to provide the microorganism-collecting chip wherein a dark filter is used as the filter for collecting microorganisms, whereby microorganisms can be quantified accurately by suppressing luminescence of a background.

The other object of the invention is to provide the microorganism-collecting chip wherein a thin film made of a certain component is formed on the filter for collecting microorganisms, whereby microorganisms can be quantified accurately by suppressing luminescence of a background.

The other object of the invention is to provide the microorganism-collecting chip wherein a film thickness of the thin film is set at an appropriate value to make surer the effect given by forming the thin film.

The other object of the invention is to provide a microorganism-collecting kit comprising the foregoing microorganism-collecting chip and a suction filtration unit.

The other object of the invention is to provide the microorganism-collecting kit wherein a negative pressure tube is used as the suction filtration unit which dispenses with the use of a device such as a pump or a special technique.

The other object of the invention is to provide the microorganism-collecting kit wherein a rubber stopper is mounted at an opening of the negative pressure tube, whereby suction can be performed by thrusting a tube through the rubber stopper from outside.

The other object of the invention is to provide the microorganism-collecting kit wherein a rubber stopper whose central portion is made of a thin layer is used, whereby a tube can easily be thrust from outside.

The other object of the invention is to provide the microorganism-collecting kit wherein a hollow needle that reaches the inside of the negative pressure tube is mounted on a lower portion of the filter for collecting microorganisms, whereby the needle penetrates the rubber stopper to easily reach the inside of the negative pressure tube.

The other object of the invention is to provide a method of quantifying microorganisms, which comprises trapping stained microorganisms on a filter for collecting microorganisms using the foregoing microorganism-collecting chip, and detecting both or either of viable cells and dead cells and specific species of microorganisms at the same time.

The other object of the invention is to provide a method of quantifying microorganisms, which comprises trapping microorganisms on a filter for collecting microorganisms using the foregoing microorganism-collecting chip, then staining the microorganisms, and detecting both or either of viable cells and dead cells and specific species of microorganisms at the same time.

The other object of the invention is to provide the method of quantifying microorganisms, wherein India ink is added to a liquid specimen to darken the filter for collecting microorganisms in trapping the microorganisms on the filter, whereby luminescence of a background or contaminants is suppressed to quantify the microorganisms with high accuracy.

The other object of the invention is to provide the method of quantifying microorganisms, wherein India ink is added from above the filter for collecting microorganisms on which the microorganisms are trapped to quantify the microorganisms with high accuracy as mentioned above.

The other object of the invention is to provide the method of quantifying microorganisms, wherein a microorganism-quantifying apparatus is confirmed to be in a normal state using a specimen for confirming a normal state of a microorganism-quantifying apparatus, and the microorganisms are then quantified without inducing inaccurate quantification results based on abnormality of the apparatus.

The other object of the invention is to provide the method of quantifying microorganisms, wherein a base material on which surface polymeric fluorescent grains are fixed is used in the specimen for confirming a normal state of the microorganism-quantifying apparatus, whereby the state of the apparatus can be confirmed accurately and repeatedly.

The other object of the invention is to provide the method of quantifying microorganisms, wherein a base material on which surface stained microorganisms are fixed is used in the specimen for confirming a normal state of the microorganism-quantifying apparatus, whereby the state of the apparatus can be confirmed accurately.

The other object of the invention is to provide a specimen for confirming a normal state of a microorganism-quantifying apparatus, wherein a base material on which surface luminous bodies that emit light with excitation light of a specific wavelength are fixed is used to confirm the state of the apparatus accurately.

The other object of the invention is to provide the specimen for confirming a normal state of a microorganism-quantifying apparatus, wherein the base material is darkened, whereby luminescence of a background is suppressed to confirm the state of the apparatus accurately.

The other object of the invention is to provide the specimen for confirming a normal state of a microorganism-quantifying apparatus, wherein a thin film made of a certain component is formed on the base material having the luminous bodies fixed thereon, whereby luminescence of a background is suppressed to confirm the state of the apparatus accurately.

The other object of the invention is to provide the specimen for confirming a normal state of a microorganism-quantifying apparatus, wherein a film thickness of the thin film is set at an appropriate value to make surer an effect given by forming the thin film.

The other object of the invention is to provide a microorganism-quantifying apparatus for quantifying microorganisms trapped on a filter for collecting microorganisms in a microorganism-collecting chip, wherein it can be confirmed that the apparatus is in a normal state.

DISCLOSURE OF THE INVENTION

A microorganism-collecting chip of the invention comprises a filter for removing contaminants and a filter for collecting microorganisms in order to attain the foregoing aims, and it is characterized in that the microorganisms are trapped on the filter for collecting microorganisms by filtration. According to the invention, the microorganism-collecting chip is obtained in which when the test sample is a special one such as food garbage or dust in the environment, contaminants such as vegetable garbage and meat slices can be removed efficiently, microorganisms which are smaller in size than these and can be passed through the filter for removing contaminants are trapped on the filter for collecting microorganisms and these trapped microorganisms are previously stained or stained after trapped to permit easy detection.

The invention is characterized in that a pore diameter of the filter for removing contaminants is set at from 5 to 20 μm and a pore diameter of the filter for collecting microorganisms is set at from 0.2 to 0.8 μm. According to the invention, the microorganism-collecting chip is obtained in which the pore diameter of the filter for removing contaminants is set at from 5 to 20 μm to remove contaminants as much as possible and the pore diameter of the filter for collecting microorganisms is set at from 0.2 to 0.8 μm to surely trap the microorganisms on the filter for collecting microorganisms.

The invention is characterized in that the filter for removing contaminants is located on a bottom of a liquid specimen injection container. According to the invention, the microorganism-collecting chip is obtained in which even a large volume of a liquid specimen can easily be filtered and the liquid specimen can easily be poured on the filter for removing contaminants.

The invention is characterized in that the liquid specimen injection container is mounted ahead of the filter for removing contaminants. According to the invention, the microorganism-collecting chip is obtained in which the liquid specimen injection container is adapted to be detachable from a site including the filter for removing contaminants, whereby the liquid specimen injection container can be used repeatedly.

The invention is characterized in that a lid with a swab for covering an opening of the liquid specimen injection container is provided. According to the invention, the microorganism-collecting chip is obtained in which microorganisms can easily be collected from a position hard to collect the microorganisms, such as a flaw on a chopping board or a corner of a test sample.

The invention is characterized in that a site including the filter for collecting microorganisms is adapted to be solely removable. According to the invention, the microorganism-collecting chip is obtained in which the site including the filter for collecting microorganisms is solely removed without the need of removing the filter only, which makes it easy to quantify the microorganisms.

The invention is characterized in that a dark filter is used as the filter for collecting microorganisms. According to the invention, the microorganism-collecting chip is obtained which can effectively prevent inhibition of accurate quantification of microorganisms due to luminescence of a background.

The invention is characterized in that a thin film made of at least one metallic component selected from gold, copper, chromium, platinum and palladium is formed on the filter. According to the invention, the microorganism-collecting chip is obtained which can effectively prevent inhibition of accurate quantification of microorganisms due to luminescence of a background.

The invention is characterized in that a film thickness of the thin film is set at from 10 to 50 nm. According to the invention, the microorganism-collecting chip is obtained which makes surer the effect given by forming the thin-film.

A microorganism-collecting kit of the invention is characterized by comprising the foregoing microorganism-collecting chip and a suction filtration unit for attaining the foregoing aims. According to the invention, the microorganism-collecting kit is obtained in which anybody can collect and quantify microorganisms easily and surely in a job site such as a food factory.

The invention is characterized in that a negative pressure tube is used as the suction filtration unit. According to the invention, the negative pressure tube is used as the suction filtration unit, whereby microorganisms can be collected easily and quickly without the need of using a special, large-sized device such as a pump.

The invention is characterized in that a rubber stopper is mounted at an opening of the negative pressure tube. According to the invention, the rubber stopper is mounted at the opening of the negative pressure tube, whereby suction can be performed by thrusting a tube through the rubber stopper from outside. Further, easy handling, such as less sliding in thrusting the tube, is possible, and a filtrate can easily be discarded after suction. Further, the microorganism-collecting kit is obtained in which the rubber stopper is used to be able to keep the sealing property of the negative pressure tube in the microorganism-collecting kit.

The invention is characterized in that a central portion of the rubber stopper at the opening of the negative pressure tube is made of a thin layer. According to the invention, the microorganism-collecting kit is obtained in which the central portion of the rubber stopper at the opening of the negative pressure tube is made of the thin layer, whereby a hollow needle or the like can be thrust with less resistance.

The invention is characterized in that a hollow needle that reaches the inside of the negative pressure tube is mounted on a lower portion of the filter for collecting microorganisms in the microorganism-collecting chip. According to the invention, the microorganism-collecting kit is obtained in which the hollow needle is mounted to make easy the suction filtration of the liquid specimen located above the hollow needle.

A method of quantifying microorganisms in the invention is, for attaining the foregoing aims, characterized by comprising contacting a liquid specimen with one or more of a first compound that colors viable and dead cells, a second compound that colors the dead cells with a wavelength different from that of the foregoing coloration and a third compound that colors the viable cells with a wavelength different from that of the foregoing coloration and at least one fourth compound that allows coloration with a wavelength different from that of the foregoing coloration by a reaction with a specific microorganism-derived material, staining microorganisms in case of containing the microorganisms in the liquid specimen, then trapping the microorganisms on a filter for collecting microorganisms using the foregoing microorganism-collecting chip, and thereafter detecting both or either of the viable cells and the dead cells and the specific species of microorganisms at the same time from the difference in wavelength and the amount of coloration. According to the invention, the method of quantifying microorganisms is obtained in which the viable cells, the dead cells and the specific species of microorganisms can be quantified accurately and easily.

A method of quantifying microorganisms in the invention is, for attaining the foregoing aims, characterized by comprising trapping microorganisms on a filter for collecting microorganisms from a liquid specimen probably containing microorganisms using the foregoing microorganism-collecting chip, then contacting the trapped microorganisms with one or more of a first compound that colors viable and dead cells, a second compound that colors the dead cells with a wavelength different from that of the foregoing coloration and a third compound that colors the viable cells with a wavelength different from that of the foregoing coloration and at least one fourth compound that allows coloration with a wavelength different from that of the foregoing coloration by a reaction with a specific microorganism-derived material, staining the microorganisms, and thereafter detecting both or either of the viable cells and the dead cells and the specific species of microorganisms at the same time from the difference in wavelength and the amount of coloration. According to the invention, the method of quantifying microorganisms is obtained in which the viable cells, the dead cells and the specific species of microorganisms can be quantified accurately and easily with the small amounts of the first to fourth compounds even though the volume of the liquid specimen is large.

The invention is characterized in that India ink is added to a liquid specimen. According to the invention, the method of quantifying microorganisms is obtained in which even when a fine depressed line or the like is present on the filter for collecting microorganisms because of a problem in production, luminescence of a background that thereby occurs is suppressed or luminescence of contaminants is suppressed to quantify the microorganisms with high accuracy.

The invention is characterized in that after microorganisms are trapped on the filter for collecting microorganisms, India ink is added from above the filter for collecting microorganisms to blacken the filter for collecting microorganisms. According to the invention, the method of quantifying microorganisms is obtained in which the microorganisms can be quantified with high accuracy as mentioned above.

The invention is characterized in that a microorganism-quantifying apparatus is confirmed to be in a normal state by previously detecting luminous bodies that emit light with excitation light of a specific wavelength using a specimen for confirming a normal state of a microorganism-quantifying apparatus, the specimen comprising a base material on which surface the luminous bodies are fixed, and both or either of viable cells and dead cells and specific species of microorganisms are then detected at the same time. According to the invention, the method of quantifying microorganisms is obtained in which microorganisms can be quantified accurately by confirming the state of the apparatus because the luminous bodies cannot be detected accurately when the apparatus is abnormal.

The invention is characterized in that the luminous bodies are polymeric fluorescent grains. According to the invention, the method of quantifying microorganisms is obtained in which since the polymeric fluorescent grains maintain stable and uniform luminescence over a long period of time, the state of the apparatus can be accurately confirmed repeatedly and the safety to the human body is secured.

The invention is characterized in that the luminous bodies are stained microorganisms. According to the invention, the method of quantifying microorganisms is obtained in which since the luminous bodies have the same size and shape as the microorganisms to be quantified, the state of the apparatus can be confirmed accurately.

A specimen for confirming a normal state of a microorganism-quantifying apparatus in the invention is, for attaining the foregoing aims, characterized by comprising a base material on which surface luminous bodies that emit light with excitation light of a specific wavelength are fixed for confirming that the microorganism-quantifying apparatus is in a normal state before quantifying microorganisms. According to the invention, the specimen for confirming a normal state of an apparatus is obtained in which it is accurately judged whether the microorganism-quantifying apparatus is in a normal state or not.

The invention is characterized in that the base material is darkened. According to the invention, the specimen for confirming a normal state of a microorganism-quantifying apparatus is obtained in which the state of the apparatus can be confirmed accurately.

The invention is characterized in that a thin film containing at least one metallic component selected from gold, copper, chromium, platinum and palladium is formed on a base material on which surface luminous bodies that emit light with excitation light of a specific wavelength are fixed. According to the invention, the state of the apparatus can be confirmed accurately by suppressing luminescence of a background, and a luminous intensity of the luminous bodies can be adjusted, for example, a luminous intensity can be decreased when it is too high. Further, the specimen for confirming a normal state of a microorganism-quantifying apparatus is obtained in which drop of the luminous bodies fixed on the surface of the base material or the like is prevented.

The invention is characterized in that a film thickness of a thin film is set at from 10 to 1,000 nm. According to the invention, the specimen for confirming a normal state of a microorganism-quantifying apparatus is obtained in which the effect given by forming the thin film is more secured.

A microorganism-quantifying apparatus of the invention is, for attaining the foregoing aims, characterized by comprising a light source for emitting excitation light with a predetermined wavelength region to a fixed micro-area of the filter for collecting microorganisms in the foregoing microorganism-collecting chip, a light receiving unit for receiving the light of the predetermined wavelength region emitted with the excitation light, a microorganism-identifying unit for receiving the light emitted by the light source in a determined time and identifying the light as the microorganism when the amount of light received is within a determined threshold, a moving unit for moving the fixed micro-area continuously or intermittently and an addition unit for adding up the number of the microorganisms from signals identified as microorganisms by the microorganism-identifying unit, wherein a base material on which surface luminous bodies that emit light with excitation light of a specific wavelength are fixed is provided so as to be able to confirm that the microorganism-quantifying apparatus is in a normal state before quantifying the microorganisms. According to the invention, the microorganism-quantifying apparatus is obtained in which viable cells, dead cells and specific species of microorganisms can be quantified accurately and easily when the apparatus is in a normal state.

BRIEF DESCRIPTION OF THE DRAWINGS

FIG. 1 is a sectional view of an embodiment of a microorganism-collecting kit of the invention.

BEST MODE FOR CARRYING OUT THE INVENTION

Figure 2:
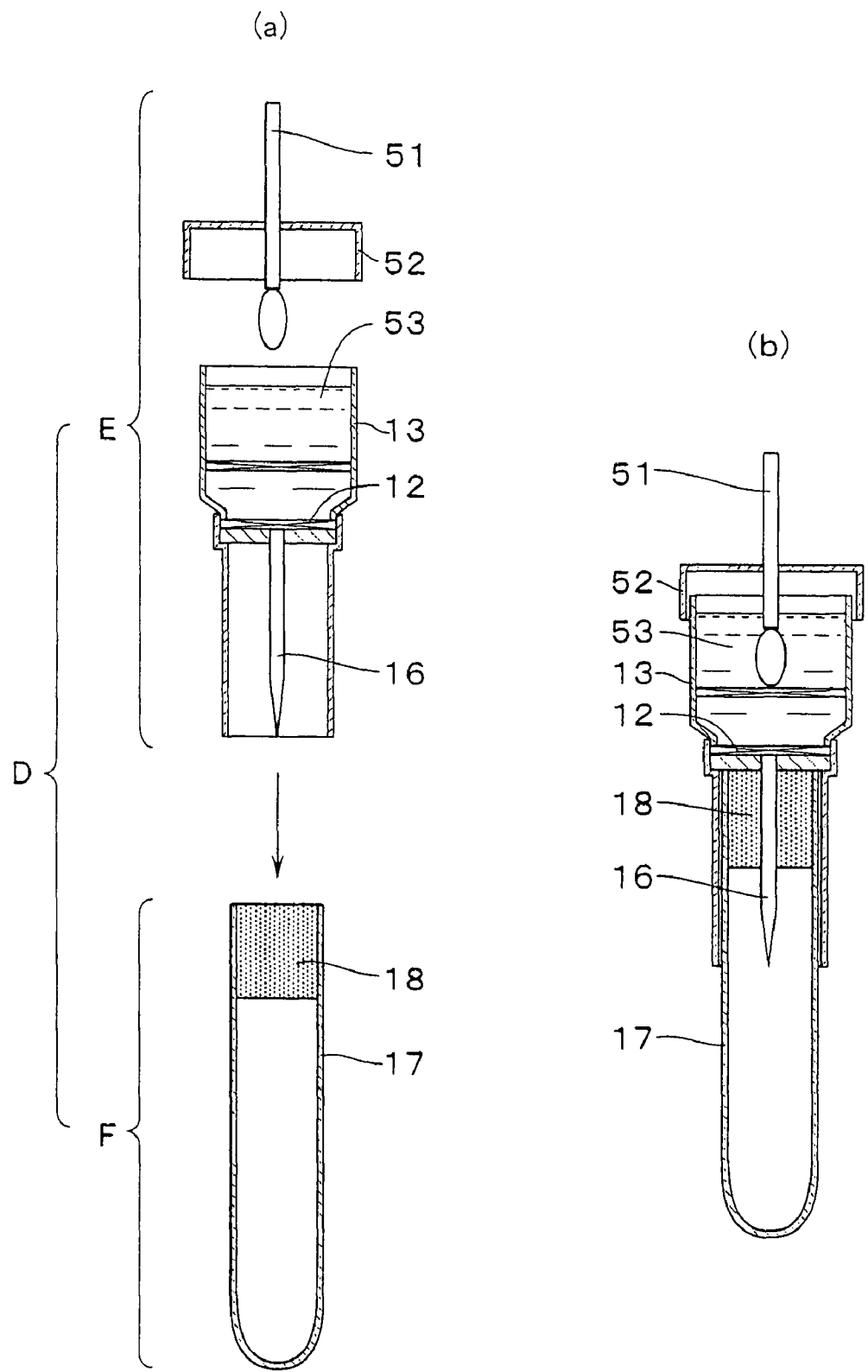
FIG. 2 is a sectional view of another embodiment of the microorganism-collecting kit of the invention.

The microorganism-collecting chip, the microorganism-collecting kit, the method of quantifying microorganisms, the specimen for confirming a normal state of a microorganism-quantifying apparatus and the microorganism-qualifying apparatus in the invention are described below by referring to the drawings. However, these are not limited at all by the following description.

FIG. 1(a) is a sectional view of an embodiment of the microorganism-collecting kit of the invention. Microorganism-collecting kit A comprises microorganism-collecting chip B and suction filtration unit C. Microorganism-collecting chip B basically comprises filter 1 for removing contaminants mounted at a front stage as a prefilter, and dark (for example, black) filter 2 for collecting microorganisms (for example, a carbon thin film is formed on a white filter) mounted at a back stage. The pore diameter of filter 1 for removing contaminants is set at from 5 to 20 μm for removing contaminants as much as possible. The pore diameter of filter 2 for collecting microorganisms is set at from 0.2 to 0.8 Mm for surely trapping microorganisms. The pore diameter here means a minimum pore diameter. Microorganism-collecting chip B has liquid specimen injection container 3, and filter 1 for removing contaminants is mounted on the bottom of liquid specimen injection container 3. Filter 2 for collecting microorganisms is mounted on seat 4, and seat 4 is held by seat holding member 5. Hollow needle 6 is integrated with seat 4 held by seat holding member 5. Liquid specimen injection container 3 and seat holding member 5 are adapted to be fitted detachably. Suction filtration unit C is negative pressure tube 7, and an opening of negative pressure tube 7 is sealed with rubber stopper 8.

A dark filter is used as filter 2 for collecting microorganisms which makes it possible to effectively prevent inhibition of accurate quantification of microorganisms due to luminescence of a background. A thin film containing at least one metallic component selected from gold, copper, chromium, platinum and palladium may be formed on the filter. These components have a quality that a spectral reflectance to excitation light of a wavelength of from approximately 300 to 550 nm is low. Accordingly, when a dark filter is used as filter 2 for collecting microorganisms and the thin film is further formed on the filter, the effect is more improved (aluminum or silver cannot be employed because the spectral reflectance to excitation light of the foregoing wavelength is high). The thin film may be made of one type of the metallic component or an alloy, a metal oxide, a metal carbide, a metal nitride, a metal carbonitride or the like. A laminated thin film is also available. As a method of forming the thin film, a known vapor growth method such as a vacuum deposition method, an ion sputtering method or an ion plating method is preferably employed. It is preferable that the film thickness of the thin film is set at from 10 to 50 nm. When it is smaller than 10 nm, the effect given by forming the thin film might not be exhibited satisfactorily. When it exceeds 50 nm, the pores of the filter might be clogged to have an adverse effect on the inherent function of the filter.

When the test sample is a liquid sample such as drinking water, it becomes itself the liquid specimen. When the test sample is a solid sample such as foodstuffs including vegetables and meat, it is homogenized to prepare a liquid specimen. Or, microorganisms are collected from its surface using a swab or the like, and released into a physiological saline or the like to prepare a liquid specimen. When a cooking tool such as a chopping board is used as a test sample, microorganisms are collected from its surface using a swab or the like, and released into a physiological saline or the like to prepare a liquid specimen. The thus-prepared liquid specimen is injected into liquid specimen injection container 3 of microorganism-collecting chip B. Hollow needle 6 is then thrust into rubber stopper 8 at the opening of negative pressure tube 7 in a negative pressure state, and hollow needle 6 is penetrated into rubber stopper 8 as shown in FIG. 1(*b*) to suction-filtrate the liquid specimen. The lower portion of seat holding member 5 is elongated to serve as a guide for surely thrusting hollow needle 6 through rubber stopper 8 of negative pressure tube 7 and to prevent a handling person from being injured with hollow needle 6.

When the liquid specimen is passed through filter 1 for removing contaminants, contaminants larger than microorganisms are removed by being trapped on filter 1 for removing contaminants. Another filter for removing contaminants may be laminated such that a filter for trapping larger contaminants such as vegetable garbage and fibers may be placed ahead of filter 1 for removing contaminants. The liquid specimen passed through filter 1 for removing contaminants reaches filter 2 for collecting microorganisms. When the liquid specimen contains microorganisms, the microorganisms are trapped on filter 2 for collecting microorganisms. A groove is formed in an interface between filter 2 for collecting microorganisms and seat 4 for uniformly spreading the liquid specimen on the whole surface of filter 2 for collecting microorganisms. Consequently, a phenomenon that microorganisms are locally concentrated and trapped on filter 2 for collecting microorganisms can be suppressed.

Liquid specimen injection container 3 and seat holding member 5 are adapted to be fitted detachably. Accordingly, after microorganisms are trapped on filter 2 for collecting microorganisms, liquid specimen injection container 3 is removed, and only the site including filter 2 for collecting microorganisms can be moved to a quantifying base of the microorganism-quantifying apparatus as shown in FIG. 1(*c*).

The liquid specimen injection container may separately be mounted ahead of the filter for removing contaminants.

The central portion of the rubber stopper at the opening of the negative pressure tube may be formed of a thin layer.

The liquid specimen can be separately prepared using a test tube or the like. It is also possible that a physiological saline or the like is previously poured into liquid specimen injection container 3 and microorganisms collected with a swab or the like are released therein to form the liquid specimen.

Liquid specimen injection container 3 and seat holding member 5 are adapted to be fitted detachably. Both of them may be joined with a screw. It is also possible that they may be integrally formed at the beginning of the production, a separation groove for easily separating them is formed in an appropriate position over an outer periphery and they are separated using this separation groove.

The length of the hollow needle is not limited so long as the hollow needle penetrates the rubber stopper and reaches the inside of the negative pressure tube.

FIG. 2(*a*) is a sectional view of another embodiment of the microorganism-collecting kit of the invention. Microorganism-collecting kit D comprises microorganism-collecting chip E and suction filtration unit F. Microorganism-collecting chip E is different from microorganism-collecting chip B shown in FIG. 1(*a*) in that lid 52 with swab 51 for covering the opening of liquid specimen injection container 13 is provided on liquid specimen injection container 13. The microorganism-collecting kit is fitted with the swab, which makes it easy and convenient to conduct sampling from a test sample with a complicated shape, such as a test sample having many flaws on the surface or a corner of a kitchen. Further, the shape is simplified by integrating swab 51 with lid 52 as in microorganism-collecting chip E. As shown in FIG. 2(*a*), physiological saline 53 is previously injected in liquid specimen injection container 13 and swab 51 is made to have a length enough to dip in physiological saline 53. Consequently, after microorganisms are collected from the test sample using swab 52, lid 52 is put on liquid specimen injection container 13, and microorganism-collecting chip E is shaken vertically and horizontally, whereby the microorganisms adhered to swab 51 are easily released into physiological saline 53 to prepare a liquid specimen.

After the microorganisms are released into physiological saline 53, hollow needle 16 is penetrated into rubber stopper 18 as shown in FIG. 2(*b*) to suction-filtrate the liquid specimen and trap the microorganisms on filter 12 for collecting microorganisms. Then, in the same manner as shown in FIG. 1(*c*), liquid specimen injection container 13 is removed, and only the site including filter 12 for collecting microorganisms is moved to a quantifying base of the microorganism-quantifying apparatus.

The swab is not necessarily integrated with the lid.

The swab is not necessarily made to have a length enough to dip in a physiological saline. Any length is available so long as the microorganisms adhered to the swab can be released into the physiological saline by shaking.

The swab may be dipped in the physiological saline at the beginning of the production of the microorganism-collecting kit. In this case, since the swab is wet with the physiological saline, the microorganisms can effectively be collected from a dry specimen in particular.

It is also possible that the microorganisms adhered to the swab are released into the physiological saline in a test tube or the like to prepare a liquid specimen and the thus-prepared liquid specimen is injected into the liquid specimen injection container.

The microorganisms trapped on the filter for collecting microorganisms in this manner can be detected and quantified by various methods. A method of detecting and quantifying both or either of viable cells and dead cells and specific species of microorganisms at the same time is described below.

The first method of quantifying microorganisms in the invention comprises contacting a liquid specimen with one or more of a first compound that colors viable and dead cells, a second compound that colors the dead cells with a wavelength different from that of the foregoing coloration and a third compound that colors the viable cells with a wavelength different from that of the foregoing coloration and at least one fourth compound that allows coloration with a wavelength different from that of the foregoing coloration by a reaction with a specific microorganism-derived material, staining microorganisms in case of containing the microorganisms in the liquid specimen, then trapping the microorganisms on a filter for collecting microorganisms using a microorganism-collecting chip, and thereafter detecting both or either of the viable cells and the dead cells and the specific species of microorganisms at the same time from the difference in wavelength and the amount of coloration. According to this method, the viable and dead cells, the viable cells, the dead cells and the specific species of microorganisms are colored with different wavelengths. Accordingly, both or either of the viable cells and the dead cells and the specific species of microorganisms can be detected at the same time from the difference in wavelength and the coloration amount.

With respect to the coloration, for example, coloration by fluorescence is mentioned. In this case, a nucleic acid-binding compound is used as the first compound, whereby the viable and dead cells can be quantified with high accuracy at a single cell level. A nucleic acid-binding compound is used as the second compound, whereby the dead cells can be quantified with high accuracy at a single cell level. A compound that colors by a reaction with a microorganism-derived substance is used as the third compound, whereby only the live microorganisms can be quantified by the difference in coloration amount. At this time, an enzyme protein is used as the microorganism-derived substance, whereby it can be judged whether the microorganisms are alive or dead, from the reactivity. Further, the enzyme protein is used as the specific microorganism-derived substance, whereby it can be judged whether the specific species of microorganisms are alive or dead, from the reactivity.

The first compound which is used for fluorescent staining of the microorganisms and which colors the viable and dead cells includes compounds which are non-specifically immersed into the membrane surface of the viable and dead cells and allow coloration by specific binding to a nucleic acid present in the cells, such as 4',6-diamidino-2-phenylindole dihydrochloride (its derivatives are also available). The second compound which colors the dead cells with a wavelength different from that of the foregoing coloration includes compounds which are non-specifically immersed into the membrane surface of the dead cells and allow coloration by specific binding to a nucleic acid present in the cells, such as propidium iodide (its derivatives are also available). The third compound which colors the viable cells with a wavelength different from that of the foregoing coloration includes compounds which are immersed into cells and allow coloration by decomposition with an enzyme protein present inviable cells, for example, an esterase, such as 6-carboxyfluorescein diacetate, 2',7'-dichlorofluoroscein diacetate, 6-(N-succinimidyloxycarbonyl)-3',6'-0,0'-diacetylfluoresce in, dihydrorhodamine, diacetofluorescein and diaceto-4-azidofluorescein (derivatives thereof are also available). The fourth compound which allows coloration with a wavelength different from that of the foregoing coloration by a reaction with the specific microorganism-derived substance includes 4-methylumbelliferyl-β-D-galactoside and 4-methylumbelliferyl-β-D-glucuronide (derivatives thereof are also available). These are decomposed by being specifically reacted with β-glucuronidase or β-galactosidase, an enzyme protein produced by *Escherichia coli* or coliform bacteria to form 4-methylumbelliferone. 4-Methylumbelliferone emits fluorescence by excitation with ultraviolet light.

The first to fourth compounds are used, for example, in a state dissolved in a physiological saline, and added to the liquid specimen to stain the microorganisms when the microorganisms are contained in the liquid specimen. The first to fourth compounds dissolved in the physiological saline may be added to the liquid specimen when in use, by storing appropriate amounts thereof in an eyedropper or the like. The staining time has to be properly determined according to the type of the test sample or the volume of the liquid specimen.

The liquid specimen containing the stained microorganisms is suction-filtrated using the microorganism-collecting kit of the invention to trap the stained microorganisms on the filter for collecting microorganisms in the microorganism-collecting chip. At this time, when a surfactant such as polysorbate 80 is added to the liquid specimen containing the stained microorganisms, the microorganisms adhered to contaminants trapped on the filter for removing contaminants and not trapped on the filter for collecting microorganisms can efficiently be passed through the filter for removing contaminants and trapped on the filter for collecting microorganisms.

Further, when a medium component such as polypeptone is added to the liquid specimen, the activity of the microorganisms can be maintained during operation. A liquid agent containing a surfactant and a medium component, for example, an LP diluent "Daigo" (trade name of a product manufactured by Nihon Pharmaceutical Co., Ltd) is preferably used for attaining such a purpose. After conducting suction filtration, only the site including filter 2 for collecting microorganisms as shown in FIG. 1(*c*) is moved to a quantifying base of the microorganism-quantifying apparatus to conduct quantification. When a polyhydric alcohol such as glycerin is added to the liquid specimen containing the stained microorganisms, it is possible to prevent deactivation of microorganisms or decay of luminescence caused by drying the surface of the filter for collecting microorganisms.

In the microorganism-collecting chip, a filter carrying the first to fourth compounds may be mounted ahead of the filter for collecting microorganisms.

Figure 3:
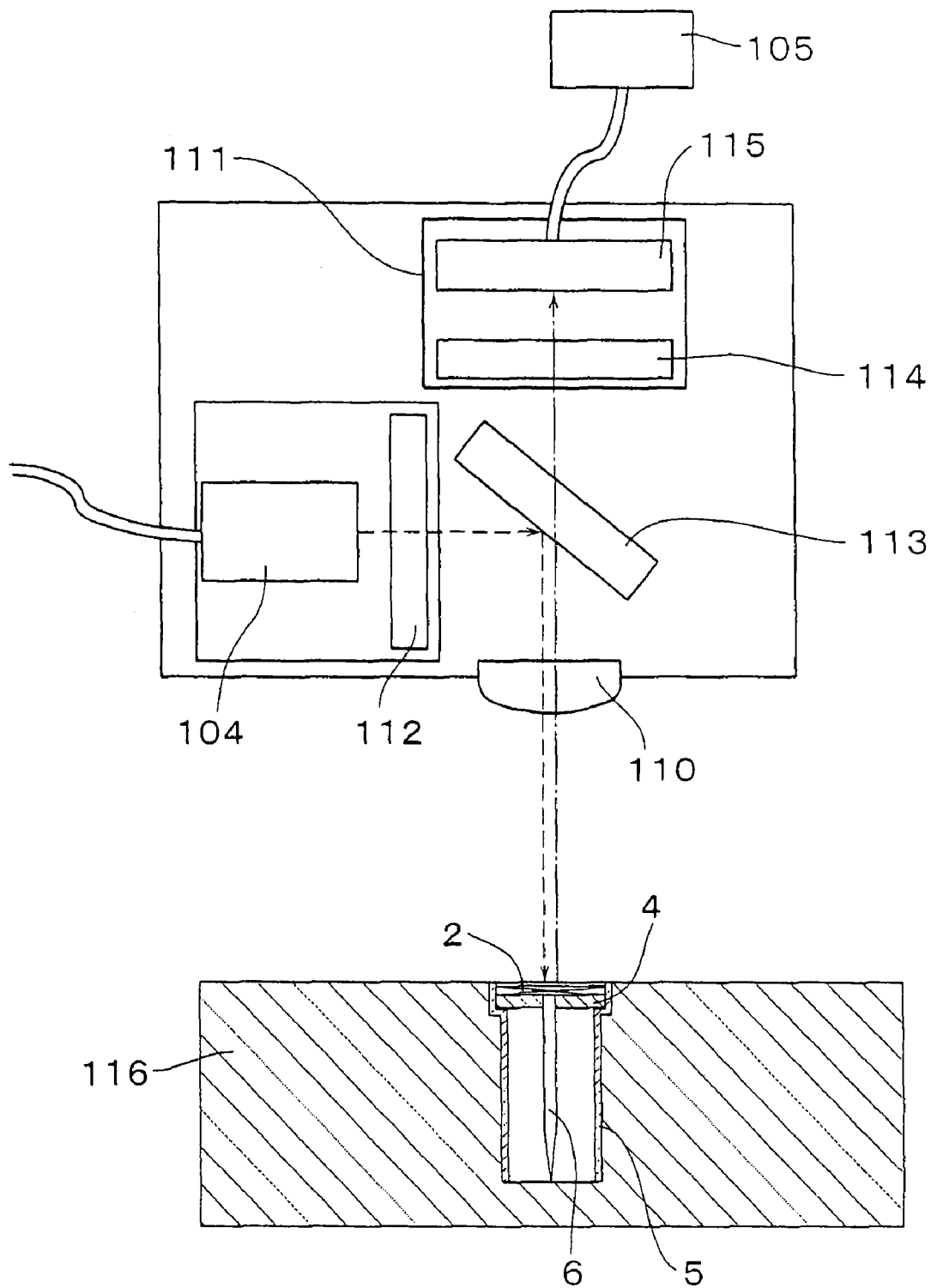
FIG. 3 is a schematic view of an embodiment of an apparatus for quantifying microorganisms using the microorganism-collecting kit of the invention.

FIG. 3 is a conceptual view showing an embodiment of the microorganism-quantifying apparatus. The microorganism-quantifying apparatus comprises light source 104, lens 110 as a light source convergence unit and light receiving portion 111. Excitation light is separated with excitation light spectral filter 112 for taking out a desired wavelength from the excitation light emitted from light source 104. A light path of the excitation light separated is changed via prism 113. The excitation light with the light path changed is converged, through lens 110, on a surface of filter 2 for collecting microorganisms of a site including filter 2 for collecting microorganisms which is mounted on inspection base 116, namely, a combination comprising filter 2 for collecting microorganisms, seat 4, seat holding member 5 and hollow needle 6. Fluorescence of microorganisms excited with excitation light is retransmitted through prism 113. At this time, fluorescence is directly transmitted through prism 113, and reaches light receiving portion 111. Fluorescence that reaches light receiving portion 111 is passed through fluorescence spectral filter 114 for taking out only desired fluorescence, and reaches photoelectric conversion element 115 embedded in light receiving portion 111 where it is converted to a signal and perceived. This microorganism-quantifying apparatus is provided with a unit that moves on inspection base 116 though not shown, whereby fluorescence on the surface of filter 2 for collecting microorganisms can be received completely or partially.

The fluorescences that have reached photoelectric conversion element 115 are identified as microorganisms or contaminants in microorganism identifying unit 105, the fluorescences identified as microorganisms are added up, and the value is quantified.

The excitation light emitted from light source 104 is converged with lens 110. At this time, regarding the range in which the excitation light is applied, the light is converged on a fixed micro-area with lens 110. In this case, the fixed micro-area indicates an area having one side ranging from 0.2 µm to 7.0 µm when determined on the basis of the size of microorganisms. Further, regarding the comparison with an agar medium diffusion method, one of methods of detecting microorganisms that have been currently most used, colonies formed of groups of microorganisms incubated and grown by the agar medium diffusion method sometimes overlap with one another when they are closely arranged. When they are finally observed visually, they might be identified as one colony. Therefore, in this case, the fixed micro-area indicates an area having one side ranging from 100 µm to 500 µm when determined on the basis of an interval at which colonies do not overlap with one another.

A time of applying the excitation light converged with lens 110 depends on a quenching time of a compound that emits fluorescence and an intensity of the excitation light. Some compounds are decomposed with ultraviolet light present in the natural world. Thus, it is advisable that the excitation light is applied within the range of from approximately 2 to 300 seconds.

When a width of a wavelength of light source 104 is wide in detecting luminescence, the excitation wavelength can be adjusted and separated with excitation light spectral filter 112. Since excitation light spectral filter 112 is changed according to a desired detection sample, it can deal with compounds that emit various fluorescences. At the same time, when a width of a wavelength of fluorescence emitted is wide, fluorescence spectral filter 114 is changed according to a desired detection sample for detecting desired luminescence. Thus, it can deal with compounds that emit various fluorescences.

Examples of light source 104 include various diodes, a halogen lamp, a xenon lamp, a cold cathode tube, lasers, black lights, a mercury lamp or the like. Of these light sources, diodes, a cold cathode tube, black lights and the like in which the maximum excitation wavelength is relatively limited can allow emission of light without using excitation light spectral filter 112 and fluorescence spectral filter 114. In a halogen lamp, a mercury lamp and the like, the use of excitation light spectral filter 112 and fluorescence spectral filter 114 is sometimes required.

Prism 113 and lens 110 have respectively a quality of transmitting ultraviolet light as required. A product having a quality of transmitting ultraviolet light includes a quartz glass and the like. They can deal with compounds which are excited with ultraviolet light. Inspection base 116 on which to mount the site including filter 2 for collecting microorganisms is rotatable. The excitation light converged with lens 110 is moved from the outer peripheral portion to the central portion of filter 2 for collecting microorganisms or from the central portion to the outer peripheral portion by a radial distance. At this time, the rotational speed of inspection base 116 is changed depending on whether the excitation light converged with lens 110 is present on the outer peripheral portion or on the central portion. Consequently, it is possible to prevent deviation of fluorescence emitted by a compound which is excited when the excitation light converged with lens 110 is present on the outer peripheral portion and on the central portion, and occurrence of afterimage and afterglow thereof.

As shown in FIG. 3, inspection base 116 has a depressed portion (installation groove) for fitting the site including filter 2 for collecting microorganisms, and the site including filter 2 for collecting microorganisms can directly be fitted thereto. At this time, for example, a metallic plate is mounted on inspection base 116 such that filter 2 for collecting microorganisms is placed thereon, and filter 2 for collecting microorganisms is fitted by being urged against the metallic plate, whereby filter 2 for collecting microorganisms is smoothly held on inspection base 116 without irregularity. As a result, microorganisms trapped on filter 2 for collecting microorganisms can be quantified more surely.

A unit for recognizing a convergence position is provided to recognize a position of the excitation light converged with lens 110, to prevent the deviation of the converged light from the orbit and to return the light to the orbit when the light is deviated from the orbit.

The fixed micro-area to which the excitation light is applied can take not only a polygonal shape including a square shape, but also a circular or elliptical shape, and the shape is not limited so long as the light can illuminate the specimen.

As a unit for separating excitation light or fluorescence, a diffraction grafting or the like may be used.

The rotational speed of inspection base 116 is adjusted to prevent afterimage and afterglow of fluorescence. It is also possible to prevent afterimage and afterglow by adjusting the moving speed of lens 110 to which the excitation light is applied.

The unit for recognizing the convergence position does not necessarily recognize the convergence position of the excitation light directly, and it is sufficient that the unit grasps the orbit on filter 2 for collecting microorganisms.

The second method of quantifying microorganisms in the invention comprises trapping microorganisms on a filter for collecting microorganisms from a liquid specimen probably containing microorganisms using a microorganism-collecting chip, then contacting the trapped microorganisms with one or more of a first compound that colors viable and dead cells, a second compound that colors the dead cells with a wavelength different from that of the foregoing coloration and a third compound that colors the viable cells with a wavelength different from that of the foregoing coloration and at least one fourth compound that allows coloration with a wavelength different from that of the foregoing coloration by a reaction with a specific microorganism-derived material, staining the microorganisms, and thereafter detecting both or either of the viable cells and the dead cells and the specific species of microorganisms at the same time from the difference in wavelength and the amount of coloration. According to this method, even though the volume of the liquid specimen is large, the microorganisms are collected on the filter for collecting microorganisms, and then stained. Thus, the viable cells, the dead cells and the specific species of microorganisms can be quantified accurately and easily with the small amounts of the first to fourth compounds.

India ink is added to the liquid specimen to darken the filter in collecting the microorganisms on the filter for collecting microorganisms, whereby luminescence of the background or contaminants is suppressed so as to be able to quantify the microorganisms with high accuracy. The India ink is not necessarily added to the liquid specimen, and it may be added from above the filter for collecting microorganisms on which the microorganisms have been trapped.

Figure 4:
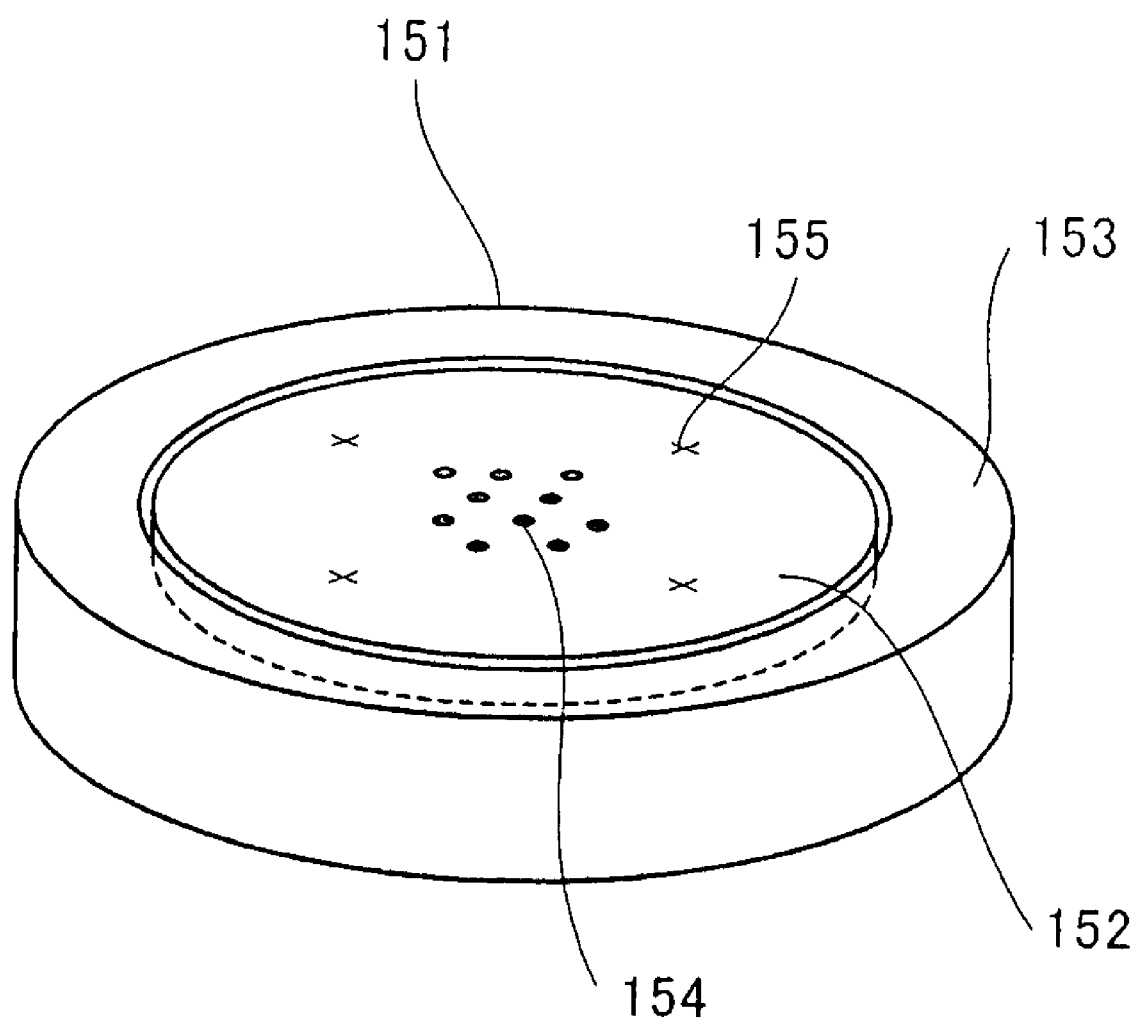
FIG. 4 is a perspective view (partially see-through view) of an embodiment of a specimen for confirming a normal state of a microorganism-quantifying apparatus of the invention.

FIG. 4 is a perspective view (partially see-through view) of an embodiment of the specimen for confirming a normal state of a microorganism-quantifying apparatus in the invention. Specimen 151 for confirming a normal state comprises base material (for example, a resin film) 152 on which surface a predetermined number of luminous bodies 154 that emit light with excitation light of a specific wavelength are fixed and a predetermined number of inclination height confirmation marks 155 are printed, and its support frame 153.

Examples of the luminous bodies fixed on the surface of the base material include polymeric fluorescent grains and stained microorganisms. Since the polymeric fluorescent grains maintain stable and uniform luminescence over a long period of time, confirmation of the state of the apparatus can repeatedly be performed accurately, and the value in use is high in that the safety to the human body is secured. The polymeric fluorescent grains are grains in which polystyrene, styrene-divinylbenzene or the like is used as a material, and which are produced by adding a fluorescent dye that emits light with excitation light of a specific wavelength in polymerization of grains. Various types of grains are commercially available. It is advisable to use polymeric fluorescent grains having a grain size of from 0.1 to 1.0 μm. When the size is too small, the number of grains can hardly be measured with high accuracy. When a filter for collecting microorganisms is employed as a base material as will be described later, the polymeric fluorescent grains might be dropped from pores of the filter. Thus, the processability as the specimen is decreased. Meanwhile, when the size is too large, the luminous intensity is too high, which might have an adverse effect on accuracy of measurement. With respect to the polymeric fluorescent grains, polymeric fluorescent grains of one type may be fixed, or polymeric fluorescent grains of plural types that emit lights with different colors by excitation lights of different wavelengths, for example, polymeric fluorescent grains that emit blue light by excitation light having a wavelength of from 350 to 400 nm and polymeric fluorescent grains that emit red light by excitation light having a wavelength of from 500 to 550 nm, may be fixed.

When the stained microorganisms are fixed on the surface of the base material, the microorganisms to be fixed are properly selected from among viable cells, dead cells and a mixture of viable cells and dead cells depending on whether the microorganisms to be tested are viable cells, dead cells or both of them (for example, when the microorganisms to be tested are dead cells, it is required to confirm a normal state of a light source for quantifying dead cells, and therefore dead cells have to be fixed on the base material). When viable cells or a mixture of viable cells and dead cells is fixed, attention is to be drawn to the fact that the safety to the human body during operation must be secured.

The base material may be a resin film, a glass, paper or a metal. The filter for collecting microorganisms may be used as the base material. When the filter for collecting microorganisms is used as the base material, the luminous bodies that emit light with excitation light of a specific wavelength can easily be trapped on the filter, namely, be fixed on the surface of the base material by filtration. It is advisable to darken (for example, blacken) the base material. This is because luminescence of the background is suppressed to be able to accurately confirm the state of the apparatus. A thin film containing at least one metallic component selected from gold, copper, chromium, platinum and palladium is formed on the base material on which surface the luminous bodies that emit light with the excitation light of the specific wavelength have been fixed. These components have a quality that the spectral reflectance to the excitation light having a wavelength of from 300 to 550 nm is low. Therefore, when the base material is darkened, further, when the foregoing thin film is formed on the base material on which surface the luminous bodies that emit light with the excitation light of the specific wavelength, the effect is more improved (aluminum or silver cannot be employed because the spectral reflectance to the excitation light of the foregoing wavelength is high). The formation of such a thin film makes it possible to adjust the luminous intensity of the luminous bodies, for example, to weaken the luminous intensity when the luminous intensity is high, and also to prevent dropping of the luminous bodies fixed on the surface of the base material. The thin film may be made of one type of the metallic component, or of an alloy, a metal oxide, a metal carbide, a metal nitride, a metal carbonitride or the like. A laminated thin film is also available. As a method of forming a thin film, a known vapor growth method such as a vacuum deposition method, an ion sputtering method or an ion plating method is preferably employed. The film thickness of the thin film is preferably from 10 to 1,000 nm, more preferably from 20 to 100 nm. The reasons are as follows. When it is less than 10 nm, the effect given by forming the thin film might not be exhibited satisfactorily. Meanwhile, when it exceeds 1,000 nm, it is difficult to measure the number of the luminous bodies fixed on the surface of the base material with high accuracy or to adjust the luminous intensity of the luminous bodies.

Figure 5:
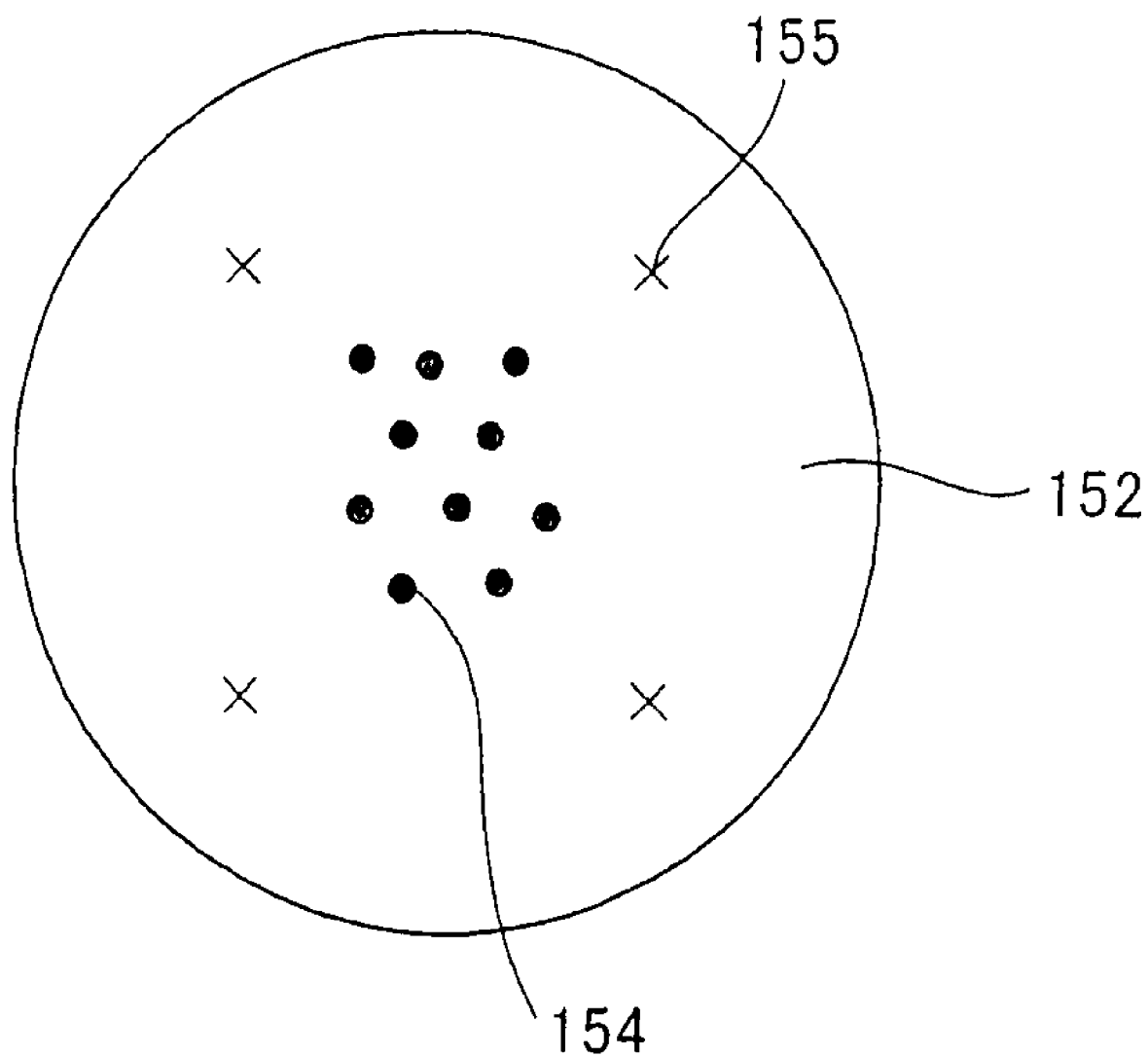
FIG. 5 is a front view of a resin film in the specimen shown in FIG. 4.

FIG. 5 is a front view of resin film 152 on which surface a predetermined number of luminous bodies 154 that emit light with excitation light of a specific wavelength are fixed and a predetermined number of inclination height confirmation marks 155 are printed as shown in FIG. 4. When the luminous bodies 154 are stained microorganisms, the microorganisms may be stained properly using, for example, the first compound that colors the viable and dead cells, the second compound that colors the dead cells and the third compound that colors the viable cells. The luminous bodies 154 can be detected with the microorganism-quantifying apparatus shown in FIG. 3. After it is confirmed that the predetermined number of the luminous bodies can be detected using the specimen for confirming the normal state, the microorganisms of the liquid specimen are quantified. When the predetermined number of the luminous bodies can be detected, the apparatus proves to be in a normal state. Meanwhile, unless the predetermined number of the luminous bodies can be detected, the apparatus does not prove to be in a normal state. Thus, the apparatus has to be adjusted or the like.

On the surface of resin film 152 shown in FIG. 5, the predetermined number of luminous bodies 154 that emit light with the excitation light of the specific wavelength are fixed, and further four inclination height confirmation marks 155 are printed. Light is applied to the four inclination height confirmation marks 155, and it is examined whether output levels of the reflected lights are uniform or not, whereby the inclination of, for example, inspection base 116 in the microorganism-quantifying apparatus shown in FIG. 3 can be inspected. Further, it is examined whether the output level meets the prescribed value or not, whereby it is possible to examine whether inspection base 116 has a prescribed height or not.

The shape of the specimen for confirming a normal state of a microorganism-quantifying apparatus in the invention is not particularly limited. For example, it is advisable that the specimen is so designed that it can be fitted into the depressed portion (installation groove) of inspection base 116 in the microorganism-quantifying apparatus shown in FIG. 3 similarly to the site including filter 2 for collecting microorganisms. Further, it is also possible that a metallic plate is mounted on inspection base 116 such that base material 152 of specimen 151 for confirming a normal state is placed thereon and base material 152 is fitted by being urged against the metallic plate, whereby base material 152 is kept smooth on inspection base 116 without irregularity to more secure the confirmation of the normal state of the apparatus.

INDUSTRIAL APPLICABILITY

As is apparent from the foregoing examples, the invention provides the microorganism-collecting chip which is characterized in that the filter for removing contaminants and the filter for collecting microorganisms are mounted in the filtration of the microorganisms from the liquid specimen to trap the microorganisms on the filter for collecting microorganisms, and which is effective for easily performing filtration of the liquid specimen prepared from a special test sample such as food garbage or dust in the environment containing large quantities of contaminants, quickening the operation and simplifying the structure.

The invention provides the microorganism-collecting kit comprising a combination of the foregoing microorganism-collecting chip and the suction filtration unit, by which anybody can quantify the microorganisms easily and surely in a job site such as a food factory.

The invention provides the method of quantifying microorganisms in which anybody can quantify the viable cells, the dead cells and the specific species of microorganisms using the foregoing microorganism-collecting kit accurately and easily.

The invention provides the specimen for confirming a normal state of a microorganism-quantifying apparatus, comprising the base material on which surface the luminous bodies that emit light with the excitation light of the specific wavelength for confirming that the apparatus is in a normal state before quantifying the microorganisms are fixed.

The invention provides the microorganism-quantifying apparatus capable of confirming that the apparatus is in a normal state using the foregoing specimen for confirming a normal state.

The invention claimed is:

1. A device for calibrating a microorganism-quantifying apparatus for use in detecting microorganisms by analyzing light from fluorescence of the microorganisms, the device comprising:
    a base material on which surface polymeric fluorescent grains are fixed;
    a thin film containing at least one metallic component selected from the group consisting of gold, copper, platinum and palladium, for reducing spectral reflectance to excitation light of a wavelength of from 300 to 550 nm, wherein the film thickness of the thin film is from 10 to 1,000 nm, formed covering the base material and the polymeric fluorescent grains wherein the fluorescent grains are between the base material and the thin film; and
    wherein the device is constructed such that excitation light from the microorganism-quantifying apparatus first enters through the thin film.

2. The device for calibrating a microorganism-quantifying apparatus according to claim 1, wherein the base material is darkened.

* * * * *

UNITED STATES PATENT AND TRADEMARK OFFICE
CERTIFICATE OF CORRECTION

PATENT NO. : 7,947,224 B2
APPLICATION NO. : 11/889106
DATED : May 24, 2011
INVENTOR(S) : Yoshikazu Tashiro et al.

Page 1 of 1

It is certified that error appears in the above-identified patent and that said Letters Patent is hereby corrected as shown below:

On the Cover Page, item (73) of the Assignee:
"Matsushita Ecology Systems Co., Ltd." should be --Panasonic Ecology Systems Co., Ltd.--.

On the Cover Page, insert: item
--(30) Foreign Application Priority Data
July 30, 2001 (JP)          2001-230054
March 22, 2002 (JP)         2002-081015--.

Signed and Sealed this
Fourth Day of October, 2011

David J. Kappos
*Director of the United States Patent and Trademark Office*